(12) United States Patent
Niver

(10) Patent No.: US 10,660,670 B1
(45) Date of Patent: May 26, 2020

(54) CERVICAL DILATOR AND METHOD OF DILATION

(71) Applicant: Gynekare, LLC, Port Huron, MI (US)

(72) Inventor: Karen L. Niver, Port Huron, MI (US)

(73) Assignee: Gynekare, LLC, Port Huron, MI (US)

( * ) Notice: Subject to any disclaimer, the term of this patent is extended or adjusted under 35 U.S.C. 154(b) by 0 days.

(21) Appl. No.: 16/570,030

(22) Filed: Sep. 13, 2019

(51) Int. Cl.
*A61B 17/42* (2006.01)
*A61M 29/02* (2006.01)
*A61M 25/10* (2013.01)

(52) U.S. Cl.
CPC ............ *A61B 17/42* (2013.01); *A61M 29/02* (2013.01); *A61B 2017/4225* (2013.01); *A61M 25/10181* (2013.11); *A61M 25/10186* (2013.11); *A61M 2029/025* (2013.01); *A61M 2210/1433* (2013.01)

(58) Field of Classification Search
CPC ... A61M 29/00; A61M 25/1002; A61B 17/42; A61B 2017/4225
See application file for complete search history.

(56) References Cited

U.S. PATENT DOCUMENTS

| | | | |
|---|---|---|---|
| 5,562,620 A | 10/1996 | Klein et al. | |
| 5,643,311 A | 7/1997 | Smith et al. | |
| 5,919,145 A | 7/1999 | Sahatjian | |
| 5,947,991 A | 9/1999 | Cowan | |
| 6,048,330 A | 4/2000 | Atala | |
| 6,258,024 B1 | 7/2001 | van Der Weegen | |
| 6,461,370 B1 | 10/2002 | Gray et al. | |
| 6,827,703 B1 | 12/2004 | Ackerman | |
| 6,960,186 B1 | 11/2005 | Fukaya et al. | |
| 7,105,007 B2 | 9/2006 | Hibler | |
| 7,220,252 B2 | 5/2007 | Shah | |
| 7,549,997 B2 | 6/2009 | Davis, Jr. | |

(Continued)

FOREIGN PATENT DOCUMENTS

WO 200168181 A1 9/2001
WO 2004047616 A2 1/2005

(Continued)

OTHER PUBLICATIONS

Arsenijevic et al., "Continuous controllable balloon dilation: a novel approach for cervix dilation," Trials 2012, 13:196, 7 pages. <http://www.trialsjournal.com/content/13/1/196>.

*Primary Examiner* — Sarah W Aleman
(74) *Attorney, Agent, or Firm* — Young Basile Hanlon & MacFarlane, P.C.

(57) ABSTRACT

A cervical dilator and methods of using the cervical dilator include guiding a shaft and a balloon of the cervical dilator through a cervix to seat the balloon in an uninflated state within a cervix. Seating the balloon includes locating proximal and distal ends of the balloon near proximal and distal ends of the cervix such that the balloon fills a canal of the cervix. After seating the balloon within the canal of the cervix, the method includes introducing a predetermined amount of fluid into the balloon cavity to fill the balloon to an inflated state. While the balloon is in the inflated state, the method includes waiting a predetermined time period to allow cervical dilation. After waiting the predetermined time period, the method includes applying light tension to the exterior surface of the shaft to remove the shaft and the balloon in the inflated state from the cervix.

12 Claims, 9 Drawing Sheets

(56) References Cited

U.S. PATENT DOCUMENTS

| | | | |
|---|---|---|---|
| 7,708,716 B2 | 5/2010 | Shah | |
| 7,763,033 B2 | 7/2010 | Gruber et al. | |
| 7,862,577 B2 | 1/2011 | Gray et al. | |
| 8,080,031 B2 | 12/2011 | Isham | |
| 8,097,014 B2 | 1/2012 | Borkon | |
| 8,784,602 B2 | 7/2014 | Schaeffer et al. | |
| 8,834,487 B2 | 9/2014 | Gruber et al. | |
| 2004/0116955 A1 | 6/2004 | Foltz et al. | |
| 2005/0055043 A1 | 3/2005 | Foltz et al. | |
| 2006/0271092 A1* | 11/2006 | Reed | A61M 29/02 606/193 |
| 2008/0077054 A1* | 3/2008 | Feuer | A61B 1/32 600/591 |
| 2008/0109010 A1 | 5/2008 | Feuer et al. | |
| 2008/0200872 A1* | 8/2008 | Isham | A61M 25/1002 604/96.01 |
| 2008/0319472 A1* | 12/2008 | Shelley | A61B 17/42 606/193 |
| 2010/0145224 A1 | 6/2010 | Lee et al. | |
| 2013/0245664 A1* | 9/2013 | Niver | A61M 29/02 606/193 |
| 2015/0297872 A1* | 10/2015 | Carpenter | A61N 5/1077 600/1 |
| 2016/0310707 A1* | 10/2016 | Ghodsian | A61M 29/02 |

FOREIGN PATENT DOCUMENTS

| | | |
|---|---|---|
| WO | 2008089516 A1 | 7/2008 |
| WO | 2008027292 A2 | 4/2009 |
| WO | 2015030726 A1 | 3/2015 |
| WO | 2016040610 A1 | 3/2016 |

* cited by examiner

CERVICAL DILATOR AND METHOD OF DILATION

TECHNICAL FIELD

This disclosure relates generally to an apparatus and method for cervical dilation. More specifically, this disclosure relates to atraumatic uterine sounding and cervical dilation using a single device with controllable inflation levels to quickly, efficiently, and safely dilate a cervix of a patient.

BACKGROUND

FIG. 1 shows a top view of a set of rods 12a-f of increasing diameter used for cervical dilation. The rods 12a-f are generally metallic and rigid and come in sets of six pieces, with each of the rods 12a-f including two distinct diameters, a different diameter for each end of the respective rod 12a-f. Thus, the set of rods 12a-f includes twelve total diameters that graduate from a smallest size, for example, 4 mm to 6 mm, in rod 12a to a largest size, for example, 9 mm to 11 mm, in rod 12f. Practitioners performing cervical dilation, such as obstetricians and gynecologists, must insert and remove the rods 12a-f in a graduated order from rod 12a to rod 12f to dilate a cervix of a patient and allow easier access to a uterus of the patient, for example, to investigate uterine bleeding or perform various procedures within the uterus. The use of the set of rods 12a-f to dilate the cervix may take several minutes, is subject to error given a possible out of sequence insertion process, and can expose the patient to twelve separate insertions, each of which may cause damage to the vagina, the cervix, the uterus, or the bowel of the patient, perforate or puncture major blood vessels proximate to these organs, and/or introduce a source of infection to the patient during the twelve-step dilation process.

FIG. 2 shows a cross-sectional view of pelvic anatomy of a patient undergoing the process of cervical dilation using rod 12a of FIG. 1. Though rod 12a is shown, the process of cervical dilation would require inserting and removing both ends of most or all of the rods 12a-f progressing from rod 12a to rod 12f. The rod 12a is being inserted into a cervix 14 after having passed through the patient's labia 16 and vagina 18. Directly below the vagina 18 is the patient's rectum 20, and directly above the vagina 18 is the patient's bladder 22, urethra 24, and clitoris 26. Each of the organs proximate to the vagina 18, that is, any of the rectum 20, the bladder 22, the urethra 24, and the clitoris 26, is susceptible to damage by the rod 12a, the damage taking the form of bruising, scraping, puncture, etc. This susceptibility can be twelve-fold in that both ends of several to all of the rods 12a-f are inserted and removed by the practitioner to perform cervical dilation.

FIG. 2 also shows a uterus 28, the front portion of which is the cervix 14, a middle portion of which is an endometrial canal 30, and end portion of which is a uterine fundus 31. A fallopian tube 32 extends from one side of the endometrial canal 30 to an ovary 34. Though a single fallopian tube 32 and ovary 34 are shown, pairs are generally present. Before completing dilation of the cervix 14, a practitioner may use one of the smaller rods 12a-f, such as rod 12a, to determine a total length or depth of the uterus 28, also known as "sounding" the uterus 28, by passing an end of the rod 12a through the cervix 14, along the endometrial canal 30, until the end of the rod 12a interfaces with the uterine fundus 31. Based on the solid, metallic composition of the rods 12a-f as well as the potential for operator error or misstep, the endometrial canal 30 and the uterine fundus 31 are at risk for puncture, scraping, or other injury during the sounding process. Further, during cervical dilation, any one of the rods 12a-f may inadvertently pass beyond the cervix 14 and into the endometrial canal 30 in a manner such that an end of the respective rod 12a-f impacts sides of the endometrial canal 30 or the uterine fundus 31 in a traumatic manner to cause abrasion, bleeding, puncture, etc. The existing uterine sounding and cervical dilation processes described in respect to FIG. 1 and FIG. 2 are lengthy in time, susceptible to operator error, and complicated with twelve potential instances to introduce injury or infection to the patient.

SUMMARY

Disclosed herein is a cervical dilator and methods of using the cervical dilator.

In one aspect, a cervical dilator is disclosed. The cervical dilator includes a shaft defining a shaft cavity extending from an open shaft inlet along an interior surface of the shaft to a closed shaft tip. The shaft tip is configured for atraumatic interface with an interior wall of a uterus during uterine sounding. The cervical dilator also includes a balloon having a first end fluidly sealed to an exterior surface of the shaft at a first location proximate the shaft tip and a second end fluidly sealed to the exterior surface of the shaft at a second location spaced from the first location. The balloon defines a balloon cavity between an interior surface of the balloon and the exterior surface of the shaft;

The cervical dilator also includes an opening defined in the shaft at a third location. The third location is closer to the first location than the second location and the opening fluidly couples the shaft cavity and the balloon cavity. The cervical dilator also includes a support disposed within the shaft cavity. The support extends from the shaft inlet to the shaft tip and is configured to provide feedback to a user of the cervical dilator during uterine sounding. The cervical dilator also includes markings spaced along an exterior surface of the shaft proximate to the second location and outside of the balloon cavity. The markings are configured to allow measurement of uterine depth during uterine sounding.

The cervical dilator includes a connector coupled to the shaft inlet. The connector includes a connector inlet configured for fluidly sealed coupling to a fluid source outlet, a connector outlet configured for fluidly sealed coupling to the shaft inlet, a connector body extending between the connector inlet and the connector outlet, and a valve disposed in the connector body that controls passage of fluid between the connector inlet and the connector outlet. The cervical dilator is configured to dilate a cervix upon a user locating the first end of the balloon in or near a distal end of the cervix, locating the second end of the balloon in or near the proximal end of the cervix, and inflating the balloon to a predetermined inflation level with fluid supplied from the fluid source outlet of a fluid source.

In another aspect, a method of cervical dilation using a cervical dilator including a shaft and a balloon sealed to the shaft is disclosed. The method includes guiding a shaft and the balloon of the cervical dilator through a cervix until a shaft tip at a first end of the shaft interfaces with an interior wall of a uterus during uterine sounding as determined based on tactile feedback provided by a support disposed within the shaft. When the shaft tip interfaces with the interior wall of the uterus, the method includes stopping the guiding and grasping an exterior surface of the shaft of the cervical dilator at a measurement location proximate a proximal end of the cervix. The measurement location includes markings spaced along the exterior surface of the shaft.

The method also includes, while grasping the exterior surface of the shaft of the cervical dilator at the measurement location, removing the shaft and the balloon from the cervix until the markings at a grasped portion of the measurement location can be viewed to determine a length or depth of the uterus. The method also includes, after determining the length or depth of the uterus, re-guiding the shaft and the balloon of the cervical dilator through the cervix to seat the balloon within the cervix. A first end of the balloon is fluidly sealed to the exterior surface of the shaft proximate the shaft tip and a second end of the balloon is fluidly sealed to the exterior surface of the shaft at a location proximate the markings.

The balloon defines a balloon cavity between an interior surface of the balloon and the exterior surface of the shaft, and the shaft defines a shaft cavity extending from a shaft inlet along an interior surface of the shaft to the shaft tip. The shaft also defines an opening at a location between the first and second ends of the balloon, and the opening fluidly couples the shaft cavity and the balloon cavity. Seating the balloon includes locating the first end of the balloon in or near a distal end of the cervix and locating the second end of the balloon in or near the proximal end of the cervix.

The method also includes, after seating the balloon within the cervix, introducing a predetermined amount of fluid to the shaft inlet such that the fluid travels along the shaft cavity, through the opening, and into the balloon cavity to inflate the balloon to an inflated state. The method also includes, after inflating the balloon to the inflated state, waiting a predetermined time period to allow cervical dilation, then applying light tension to the exterior surface of the shaft to remove the shaft and the balloon in the inflated state from the cervix.

In another aspect, a method of cervical dilation using a cervical dilator is disclosed. The method includes guiding a shaft and a balloon of the cervical dilator through a cervix to seat the balloon in an uninflated state within a cervix. The shaft extends from a shaft inlet to a shaft tip, a first end of the balloon is fluidly sealed to an exterior surface of the shaft proximate the shaft tip, and a second end of the balloon is fluidly sealed to the exterior surface of the shaft at a location spaced from the shaft tip. The balloon defines a balloon cavity between an interior surface of the balloon and the exterior surface of the shaft. The shaft defines a shaft cavity extending from the shaft inlet along an interior surface of the shaft to the shaft tip. The shaft also defines an opening at a location between the first and second ends of the balloon, and the opening fluidly couples the shaft cavity and the balloon cavity.

Seating the balloon includes locating the first end of the balloon in or near a distal end of the cervix and locating the second end of the balloon in or near a proximal end of the cervix such that the balloon fills a canal of the cervix. The method also includes, after seating the balloon within the canal of the cervix, introducing a predetermined amount of fluid to the shaft inlet such that the fluid travels along the shaft cavity, through the opening, and into the balloon cavity to fill the balloon to an inflated state. The method also includes, while the balloon is in the inflated state, waiting a predetermined time period to allow cervical dilation. The method also includes, after waiting the predetermined time period, applying light tension to the exterior surface of the shaft to remove the shaft and the balloon in the inflated state from the cervix.

BRIEF DESCRIPTION OF THE DRAWINGS

The disclosure is best understood from the following detailed description when read in conjunction with the accompanying drawings. It is emphasized that, according to common practice, the various features of the drawings are not to-scale. On the contrary, the dimensions of the various features are arbitrarily expanded or reduced for clarity.

DETAILED DESCRIPTION

A cervical dilator and methods for uterine sounding and cervical dilation using the cervical dilator are described herein. The described cervical dilator is disposable, easy to use, flexible, and fast when compared to known methods of uterine sounding and cervical dilation using the rods 12*a-f* of FIGS. 1-2. The cervical dilator 300 requires only one or two independent insertions into a cervix of the patient, is flexible and pliant to be atraumatic to the vagina, cervix, and uterus, and requires less time to achieve uterine sounding and cervical dilation than the rods 12*a-f* of FIGS. 1-2. The cervical dilator is described in FIGS. 3-7 and methods for use of the cervical dilator are described in FIGS. 8-9.

Figure 3:
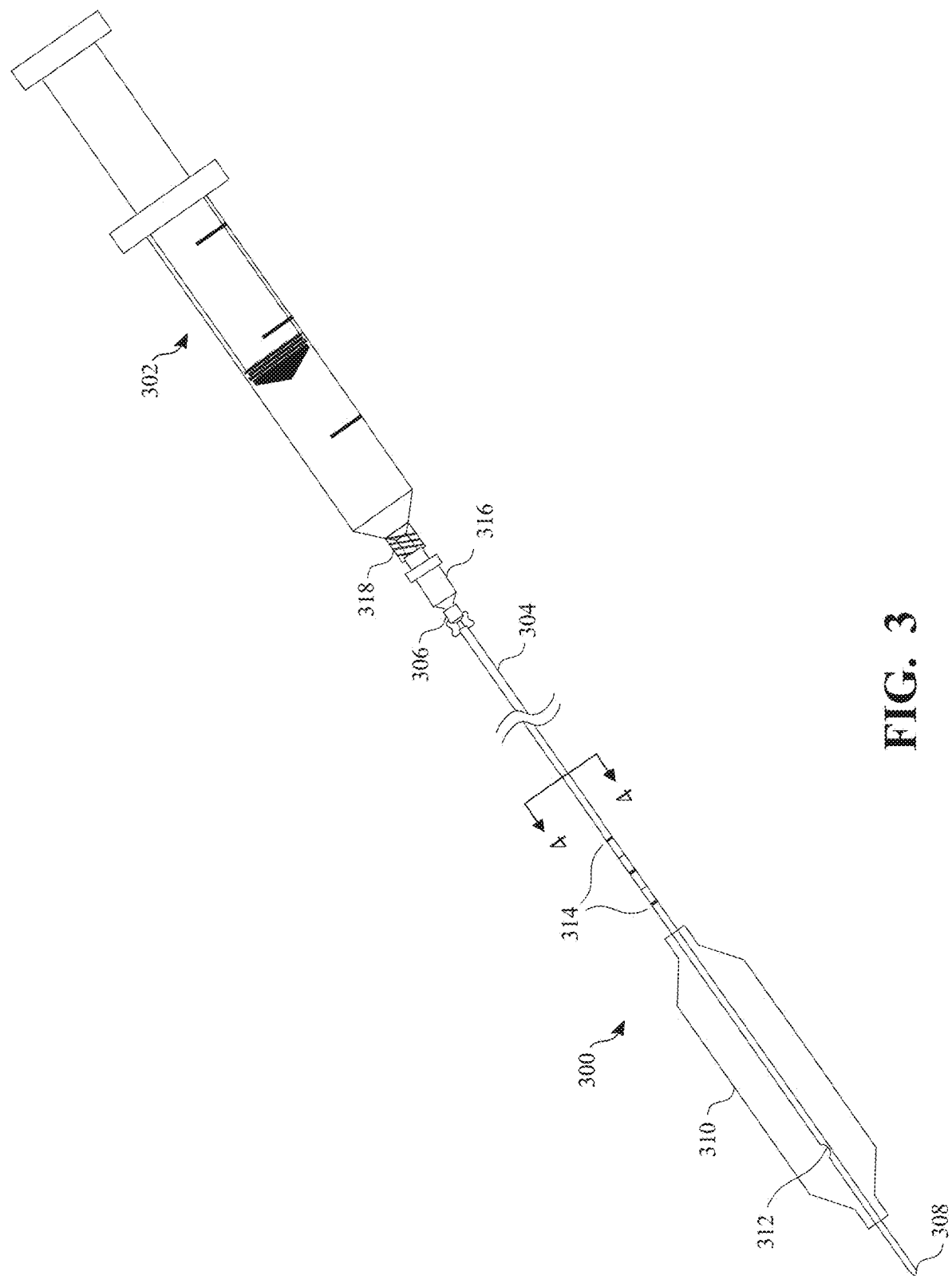
FIG. 3 shows a side view of a cervical dilator and fluid source used for uterine sounding and cervical dilation.

FIG. 3 shows a side view of a cervical dilator 300 and a fluid source 302 used for uterine sounding and cervical dilation. The cervical dilator 300 includes a shaft 304 extending from a shaft inlet 306 to a shaft tip 308, a balloon 310 shown in an inflated state, an opening 312 within the shaft 304 via which fluid passes from the fluid source 302 into the balloon 310, markings 314 spaced along an exterior of the shaft 304, and a connector 316 coupled to the shaft inlet 306. The fluid source 302, in this example, a syringe, includes a fluid source outlet 318 that is coupled to the connector 316. Detailed descriptions of various components of the cervical dilator 300 are given in FIGS. 4-7B.

Figure 1:
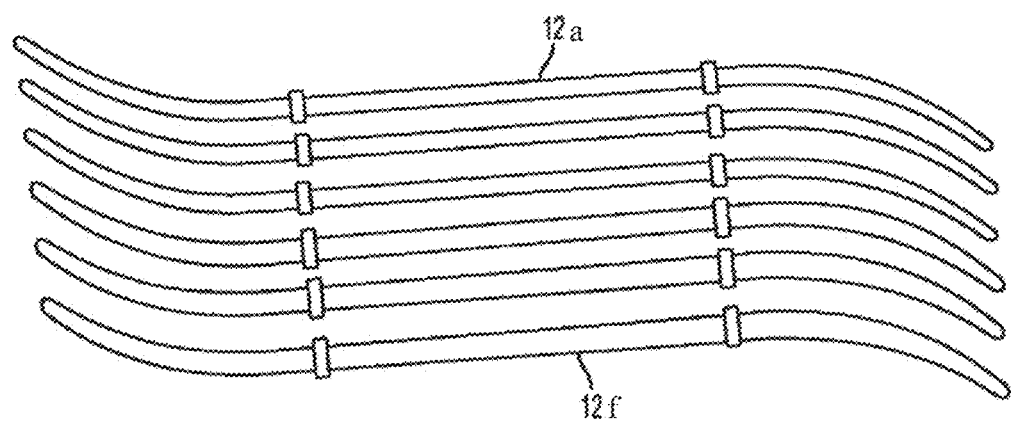
FIG. 1 shows a top view of rods 12*a-f* of increasing diameter used for uterine sounding and cervical dilation.
Figure 2:
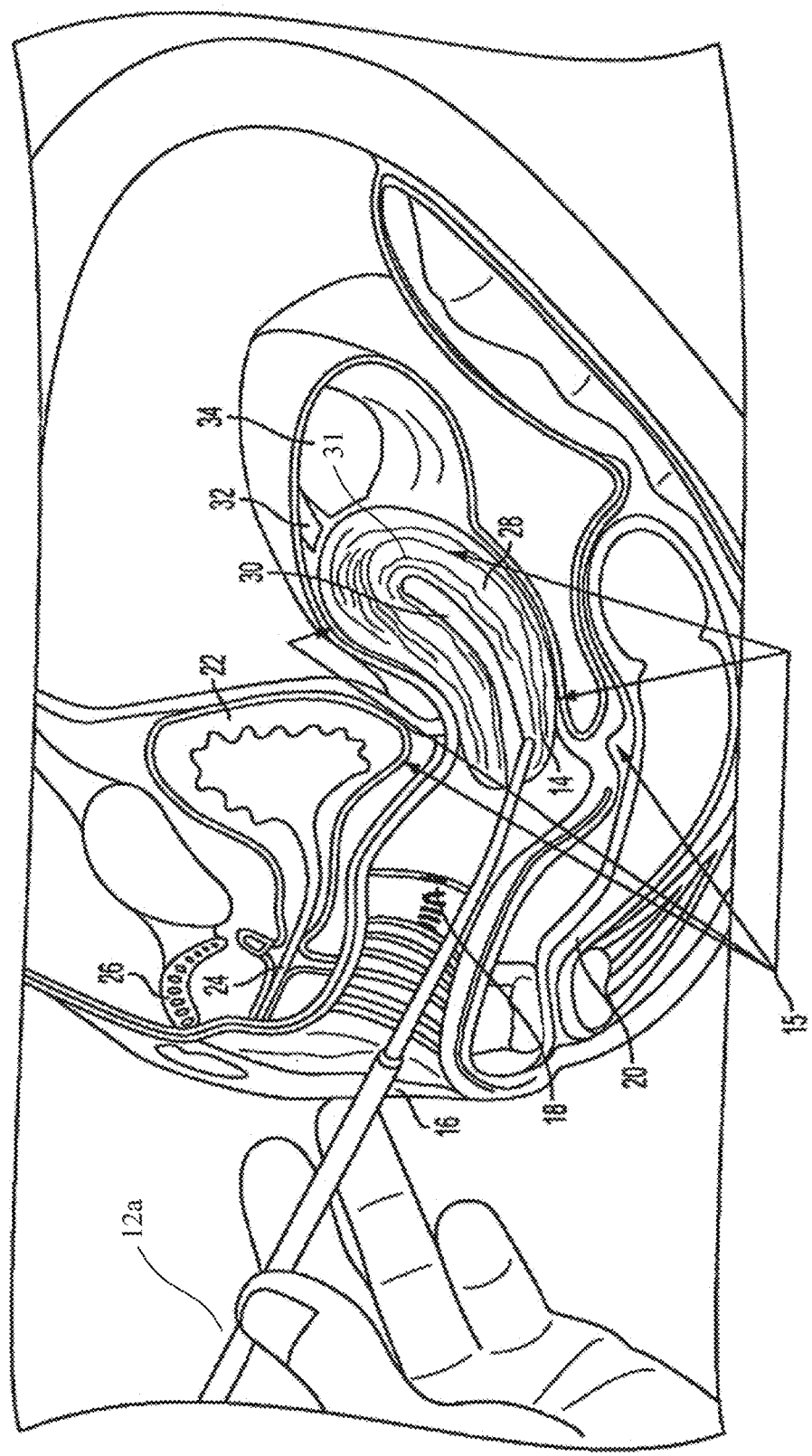
FIG. 2 shows a cross-sectional view of pelvic anatomy of a patient undergoing the process of cervical dilation using rod 12*a* of FIG. 1.

The cervical dilator 300 is configured to sound a uterus and dilate a cervix of a patient, such as the cervix 14 shown in FIG. 2, both more quickly and in a manner less prone to causing injury when compared to the rods 12*a-f* of FIG. 1. A user, e.g., a gynecologist or obstetrician, can guide the shaft 304 through the cervix until the rounded shaft tip 308 interfaces with a uterine wall of the patient and grasp the markings 314 in order to determine uterine depth, i.e. sound the uterus. After uterine sounding, the user can locate the balloon 310 in an uninflated state within a canal of the cervix. After locating the balloon 310 within the cervical canal, the user can inflate the balloon 310 with fluid, e.g. air or liquid, from the fluid source 302 in step-wise increments to a predetermined inflation level, such as the inflation level shown in the balloon 310 in FIG. 3. Detailed descriptions of methods of use of the cervical dilator 300 for uterine sounding and cervical dilation are given in FIGS. 8-9.

Figure 4:
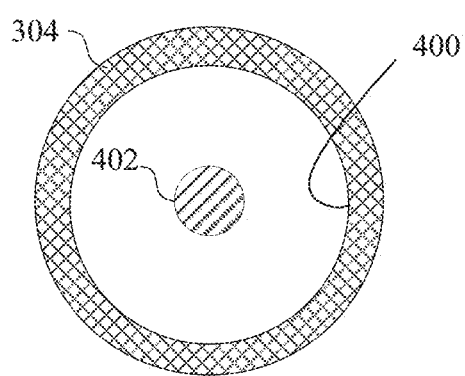
FIG. 4 shows a sectional view of the cervical dilator of FIG. 3 at location 4-4.

FIG. 4 shows a sectional view of the cervical dilator 300 of FIG. 3 at location 4-4. The shaft 304 can be formed of a flexible polymer, plastic, or other generally flexible material, such as Pellethane®, that can be sterilized for use with patients. In order to deliver fluid to and from the balloon 310 shown in FIG. 3, the shaft 304 defines a shaft cavity 400. In one example, a wall thickness of the shaft 304, that is, a distance between an inner surface of the shaft 304 that defines the shaft cavity 400 and an outer surface of the shaft 304, can vary between 0.005 in and 0.025 in. Given the thin wall of the shaft 304 and presence of the shaft cavity 400, the shaft 304 is flexible or bendable so as to be easily guided through a patient's anatomy. In one example, the shaft 304 can be designed to withstand rapid bending up to 180 degrees between temperatures of 0 to 50 Celsius without fracture.

The shaft 304 can have a length between 10 in and 14 in some embodiments and between 22 cm and 24 cm in other embodiments. Other lengths of the shaft 304 suitable for uterine sounding and cervical dilation are also possible. Given the flexibility of the shaft 304, in order to avoid floppiness and to provide the user tactile feedback, a support 402 can be disposed within the shaft cavity 400. Though shown centrally within the shaft cavity 400 in FIG. 4, the support 402 can be located along or proximate an interior wall of the shaft 304 (not shown). The support 402 can be formed, for example, of spring-tempered stainless steel, such as 304 stainless steel, or any other material that provides rigidity to the shaft 304 to promote tactile feedback while still allowing flexibility of the shaft 304. The support 402 can extend from the shaft inlet 306 to the shaft tip 308 such that impact of the shaft tip 308 with a portion of the uterine wall of a patient, such as the uterine fundus 31 of FIG. 2, is detected by tactile feedback should a user be grasping a portion of the shaft 304 proximate the connector 316 or grasping the fluid source 302 coupled to the connector 316, for example, if the user is holding the fluid source 302 as a handle for the shaft 304 of the cervical dilator 300.

Figure 5:
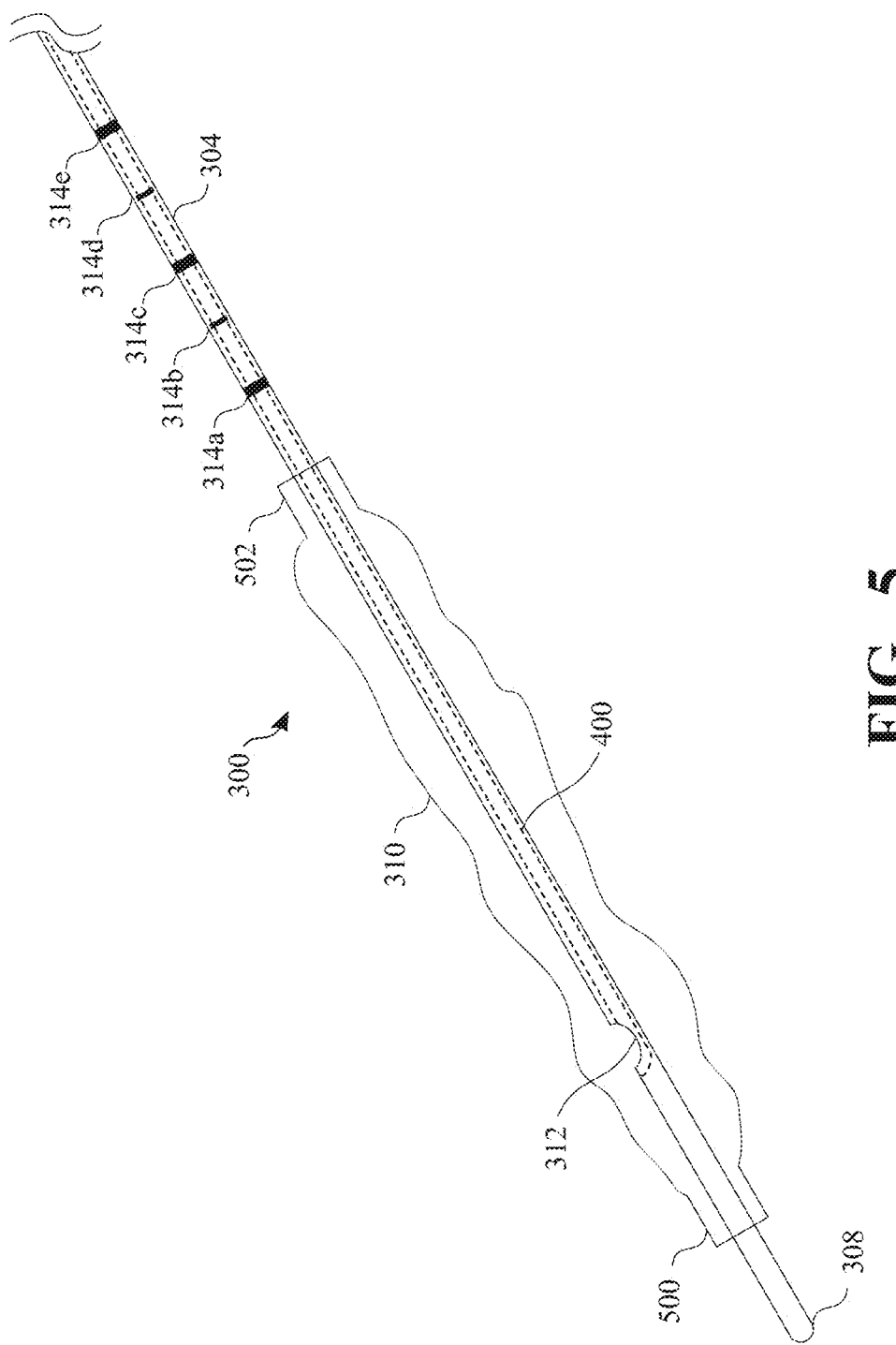
FIG. 5 shows a partial detail view of the cervical dilator of FIG. 3 with a balloon in an uninflated state.

FIG. 5 shows a partial detail view of the cervical dilator 300 of FIG. 3 with the balloon 310 in an uninflated state. The balloon 310 includes a first end 500 fluidly sealed to an exterior surface of the shaft 304 at a location proximate the shaft tip 308 and a second end 502 fluidly sealed to the exterior surface of the shaft 304 at a location spaced from the first end 500. The first and second ends 500, 502 can be adhered to the exterior surface of the shaft 304 using an adhesive such as cyanoacrylate, cyclohexanone, or any other adhesive suitable to prevent fluid from entering or exiting the balloon 310 at a location other than the opening 312. A distance between the first and second ends 500, 502 can range between 3 cm and 6 cm in some embodiments and between 4 cm and 5 cm in other embodiments. The distance between the first and second ends 500, 502 is designed such that a length of the balloon 310 along the shaft will fill an entire cervical canal in a vast majority of patients, for example, between 85 percent and 95 percent of patients.

A distance between the shaft tip 308 and the first end 500 of the balloon 310 can range between 2 mm and 10 mm in some embodiments and between 4 mm and 6 mm in other embodiments. Other distances between the shaft tip 308 and the first end 500 of the balloon 310 are also possible. The first end 500 of the balloon 310 is both proximate to the shaft tip 308 and sufficiently spaced from the shaft tip 308 to allow unencumbered use of the shaft tip 308 in guiding the shaft 304 through a cervix and in sounding a uterus. That is, the balloon 310 is spaced from the shaft tip 308 slightly so as to not interfere with guidance or sounding during use of the cervical dilator 300. In addition, the shaft tip 308 is curved so as not to scratch or puncture the uterine lining during sounding. The shaft 304 itself is also sufficiently flexible to bend the shaft tip 308 away from the uterine wall if a force over a specific threshold is exerted during uterine sounding.

The shaft 304 is shown with individually identified markings 314a-e in FIG. 5. The markings 314a-e can be spaced apart by a distance of 1 cm with the markings 314a,c,e being thicker than the markings 314b,d in order to differentiate between even and odd measures, for example, when the central-most marking 314c is located at a distance of 8 cm from the shaft tip 308. A value indicator next to each of (or some of) the markings 314a-e can be included on an exterior surface of the shaft 304 but is not shown in FIG. 5. The measurement values chosen for the markings 314a-e, such as 6 cm for marking 314a, 7 cm for marking 314b, 8 cm for marking 314c, 9 cm for marking 314c, and 10 cm for marking 314e, are chosen to cover a vast majority, for example, over 95 percent, of patients that may undergo uterine sounding and/or cervical dilation with the cervical dilator 300 of the present disclosure.

To determine uterine depth, e.g. a total length of the cervix and uterus, using the cervical dilator 300, the user grasps an exterior surface of the shaft 304 at a measurement location, that is, a location within the region covered by the markings 314a-e, after the shaft 304 of the cervical dilator 300 has been guided through the cervical canal into the uterus and the shaft tip 308 abuts a distal wall of the uterus. This grasp will also interface with or abut a proximal end or entrance of the cervix in order to properly determine the uterine depth using the cervical dilator 300. In other words, a user's fingertips may hold the shaft 304 within a region that includes the markings 314a-e while at the same time abutting the entrance of the cervix. The shaft 304 continues to be grasped while it is removed at least partially from the uterus and cervix so that the user can view the measurement location and determine which of the markings 314a-e is being grasped to identify the uterine depth of the patient undergoing uterine sounding.

Figure 6:
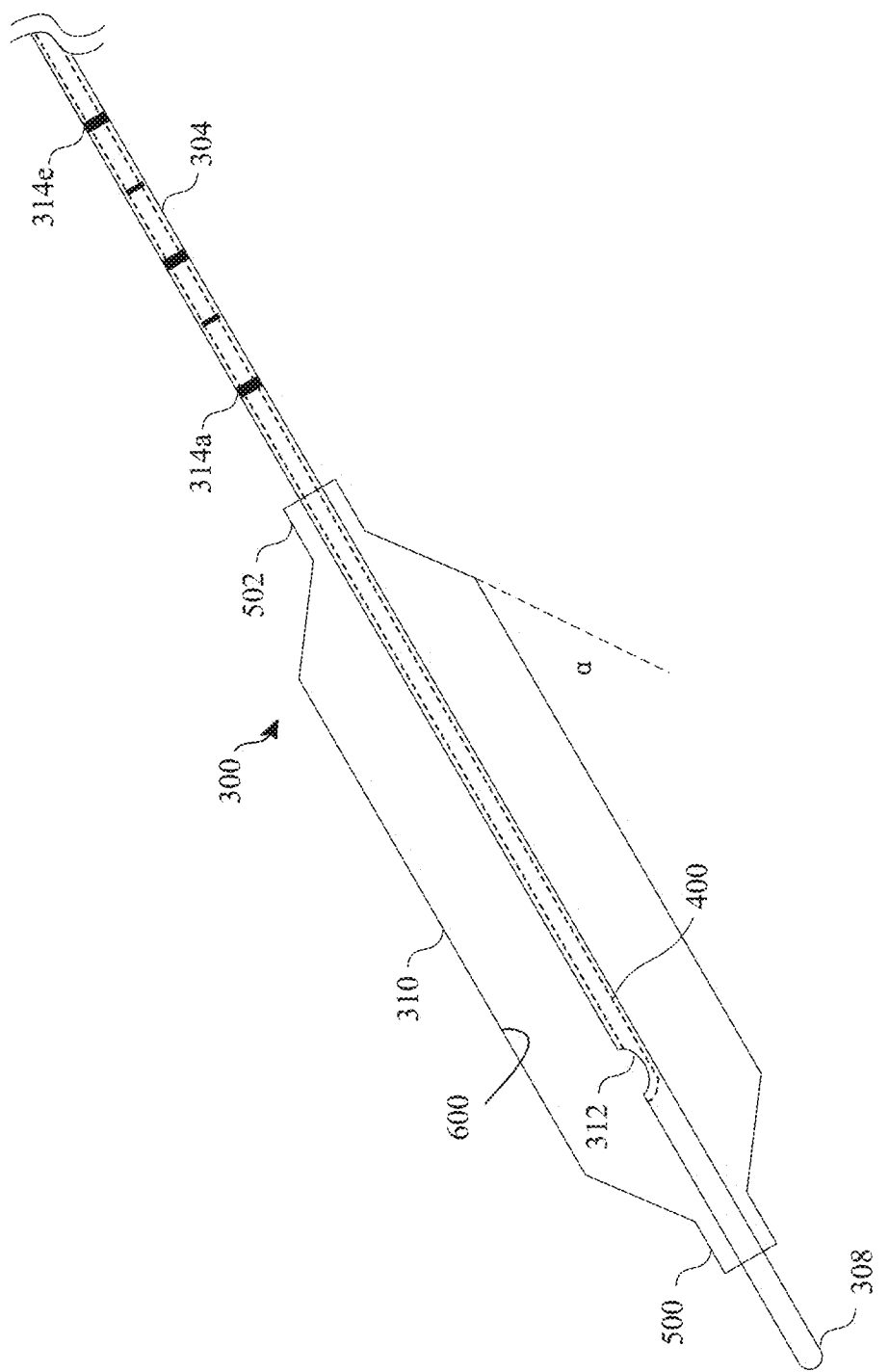
FIG. 6 shows a partial detail view of the cervical dilator of FIG. 3 with the balloon in an inflated state.

FIG. 6 shows a partial detail view of the cervical dilator 300 of FIG. 3 with the balloon 310 in an inflated state. The balloon 310 defines a balloon cavity 600 that can be filled with fluid supplied by a fluid source such as the fluid source 302 of FIG. 3. In the example where the fluid source 302 is a syringe, the syringe can be filled with a fluid such as air, water, or saline. The filled syringe can be coupled to the shaft inlet 306, and the plunger of the syringe can be plunged in a controlled manner so as to send the fluid through the shaft cavity 400, out the opening 312 in the shaft 304, and into the balloon cavity 600 to modify a state of the balloon 310 from its uninflated state shown in FIG. 5 to its inflated state shown in FIG. 6.

In the example of FIG. 6, the inflated state of the balloon 310 includes the first and second ends 500, 502 of the balloon 310 remaining both fluidly and physically sealed to the shaft 304 while a body of the balloon 310 expands outward away from the shaft 304. That is, a size of the balloon cavity 600 increases while the balloon 310 is inflated to reach the inflated state. The balloon 310 can be formed, for example, from polyurethane, urethane, polyisoprene, nylon, thermoplastic polyurethane, or another stretchable material of a low durometer sufficient to allow expansion and retraction of the balloon cavity 600 while at the same time holding an appropriate tension as needed for use of the cervical dilator 300 as both a uterine sounding device and a dilating tool. The balloon cavity 600 can be designed to have a diameter between 10 mm and 20 mm when the balloon 310 is in the inflated state. The balloon 310 can have a central portion of generally cylindrical shape in the inflated state.

A cone angle α is shown in FIG. 6 as measured between each of the first and second ends 500, 502 and a central-most portion of the balloon 310. This cone angle α can vary between 10 degrees and 30 degrees depending on a volume of fluid within the balloon cavity 600 as supplied from the fluid source 302. In one example, the cone angle α is 20 degrees. Control of the cone angle α to within the range described allows for more accurate seating of the balloon 310 within a cervical canal of the cervix since the central portion of the balloon 310 has the largest diameter and tapering at the first and second ends 500, 502 will help prevent the balloon 310 in the inflated state from inadvertently extending into a uterus at the first end 500 or a vagina at the second end 502 during use of the cervical dilator 300 for cervical dilation.

FIG. 6 also shows a location of the opening 312 within the shaft 304 as being between 15 percent and 35 percent of a distance between the first end 500 and the second end 502 of the balloon 310. The location of the opening 312 being near or proximate to the first end 500, or at least closer to the first end 500 than the second end 502, improves seating of the balloon 310 as it transitions from the uninflated state to the inflated state within the cervical canal. This improvement is due to the fluid filling the balloon cavity 600 in a manner consistent with holding the balloon 310 within cervical canal anatomy of a typical patient undergoing cervical dilation. That is, the position or location of the opening 312 in respect to the first and second ends 500, 502 of the balloon 310 allows a more efficient cervical dilation due to improved seating of the balloon 310 as the balloon 310 moves from the uninflated state to the inflated state.

Figure 7A:
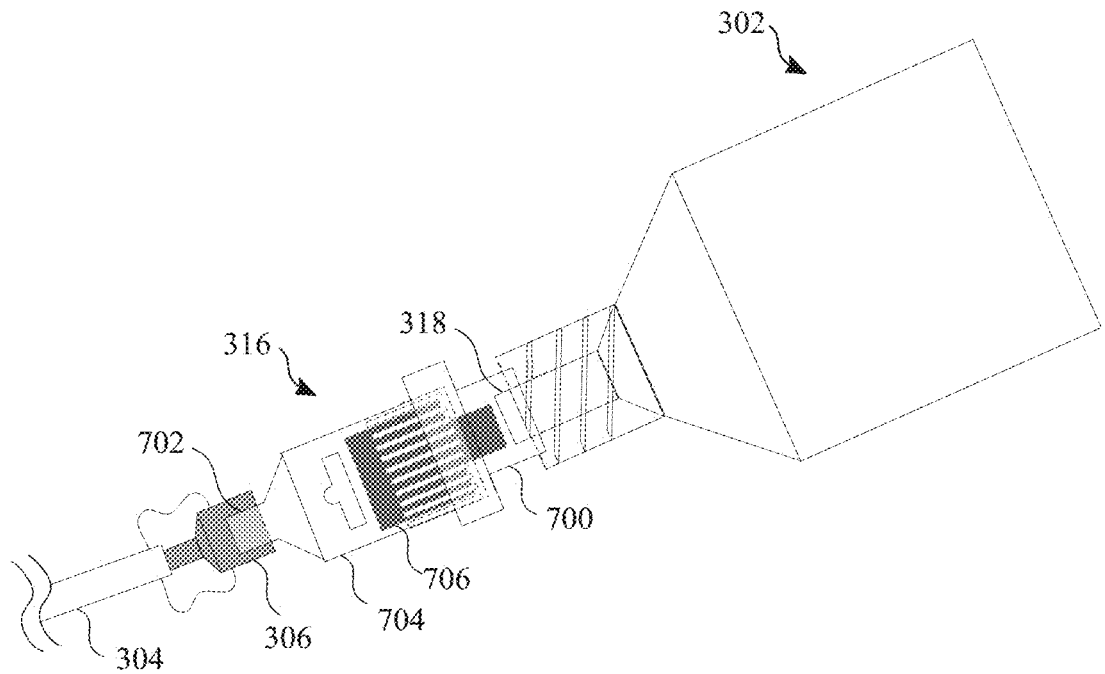
FIGS. 7A and 7B show partial detail views of a connector of the cervical dilator of FIG. 3 before inflation (FIG. 7A) and during inflation (FIG. 7B).
Figure 7B:
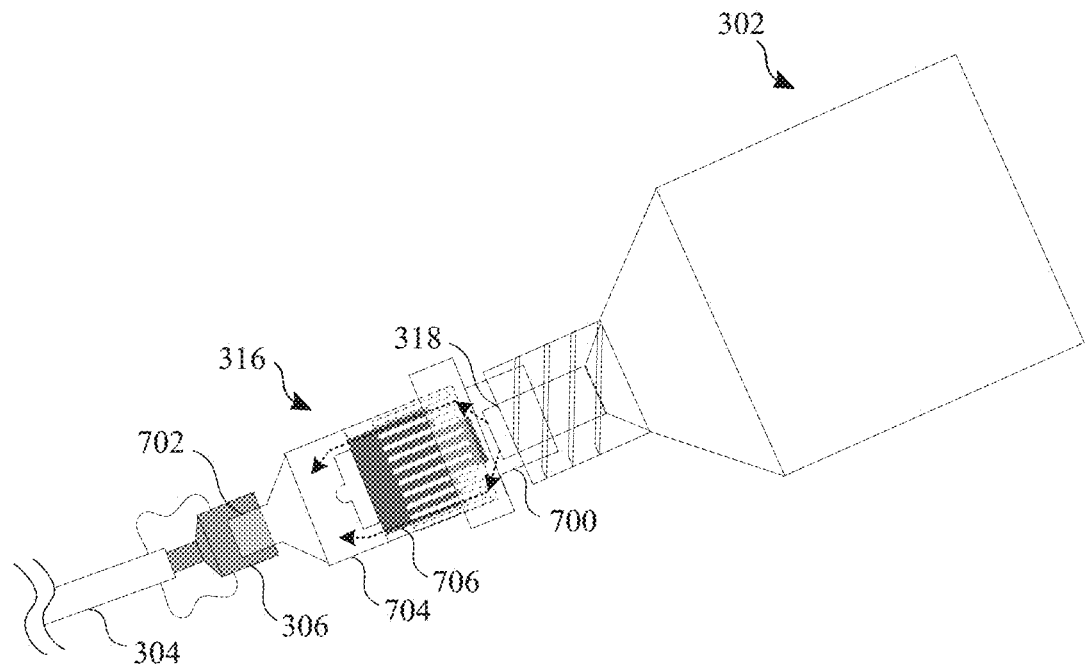

FIGS. 7A and 7B show partial detail views of the connector 316 used in the cervical dilator 300 of FIG. 3. The connector 316 includes a connector inlet 700 configured for fluidly sealed coupling to the fluid source outlet 318 of the fluid source 302. In this example, the fluid source 302 is a syringe. The connector 316 also includes a connector outlet 702 configured for fluidly sealed coupling to the shaft inlet 306. The connector 316 includes a connector body 704 extending between the connector inlet 700 and the connector outlet 702. The connector 316 also includes a valve 706 disposed in the connector body 704 that controls passage of fluid between the connector inlet 700 and the connector outlet 702. In this example, the valve 706 includes a stop cock or plunger configured to move between an open position shown in FIG. 7B and a closed position shown in FIG. 7A.

The closed position of the valve 706 shown in FIG. 7A allows the fluid source 302 (e.g., the syringe shown in FIG. 3) to be used as a hand-hold or handle for the user as the user guides the shaft 304 and the balloon 310 to various positions within a patient's anatomy. The fluid source outlet 318 can be coupled to the connector inlet 700 without the fluid source outlet 318 contacting or otherwise interfacing with the valve 706 in the connector body 704 so that the valve 706 remains in a position that blocks fluid from moving into or out of the shaft 304 and correspondingly, fluid is blocked from moving into or out of the balloon 310 (not shown) though the fluid source outlet 318 is fluidly sealed to the connector inlet 700.

The open position of the valve 706 shown in FIG. 7B allows fluid from the fluid source 302, such as air, water, or saline, to pass around the valve 706 in the connector body 704 as shown in dotted lines with arrows. In this example, the valve 706 is compressed by the fluid from the fluid source outlet 318 based on a force exerted by the fluid on the valve 706, for example, when a user presses the fluid source outlet 318 into the connector inlet 700 and engages a force-generating mechanism (such as a plunger on a syringe, not shown) to force the fluid out the fluid source outlet 318 and around the valve 706 in the connector body 704. Though fluid is shown as moving right to left in FIG. 7B using the dotted line arrows, the valve 706 can be configured to allow a reverse fluid flow direction, for example, when the fluid source 302 applies suction to the connector inlet 700 should the amount of fluid being sent to the balloon 310 through the shaft 304 need to be reduced or the balloon 310 deflated.

Figure 8:
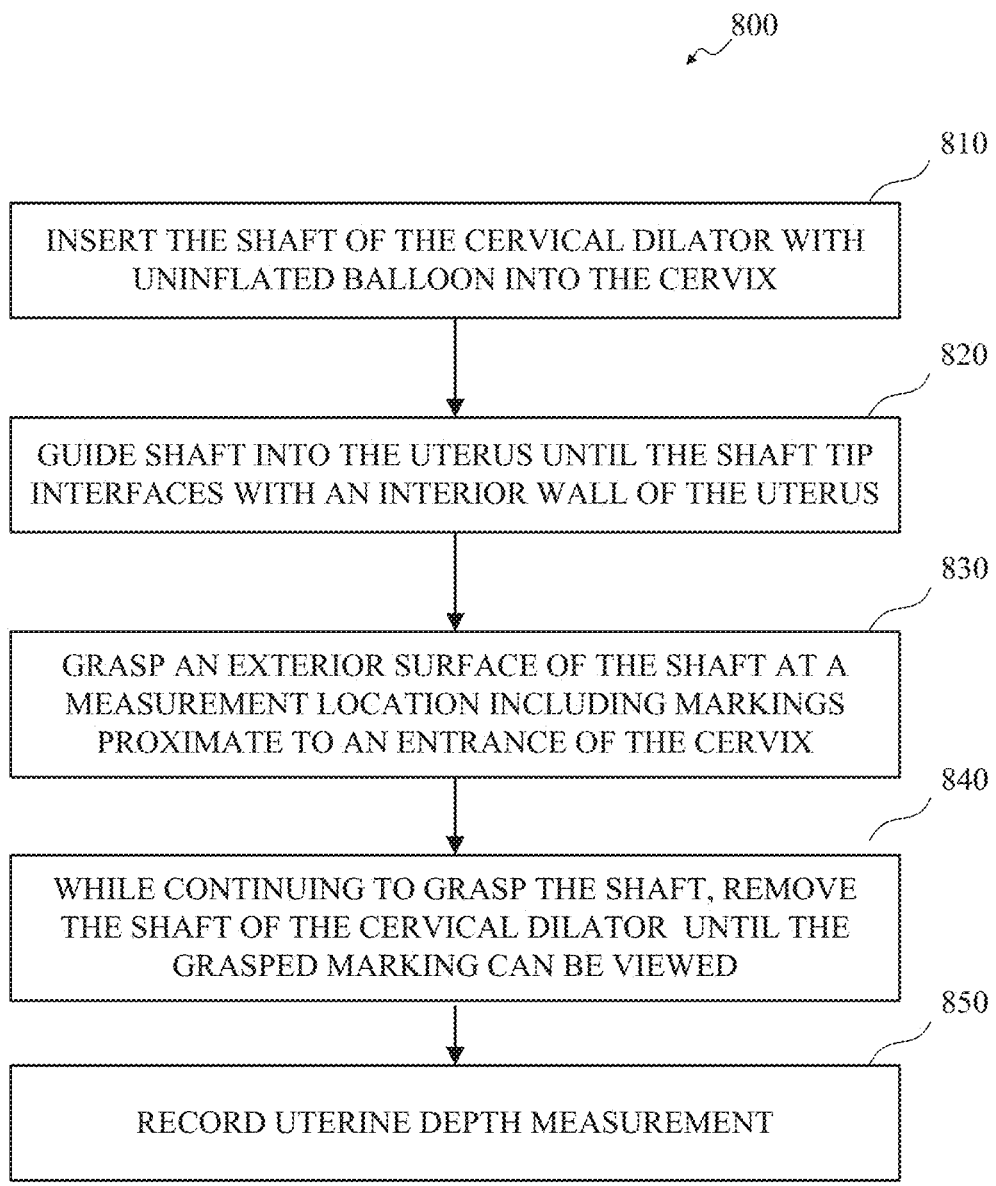
FIG. 8 shows a flowchart describing a uterine sounding method using the cervical dilator of FIG. 3.

FIG. 8 shows a flowchart describing a uterine sounding method 800 using the cervical dilator 300 of FIG. 3. The uterine sounding method 800 can be performed, for example, by a user such as a gynecologist or obstetrician seeking to determine a depth of a uterus of a patient prior to performing an intra-uterine procedure such as ablation or dilation and curettage. In a first step 810, the user can insert the shaft 304 of the cervical dilator 300 with the balloon 310 in the uninflated state into a cervix of the patient. In a second step 820, the user can guide the shaft 304 and the balloon 310 of the cervical dilator 300 through the cervix until the shaft tip 308 at a first end of the shaft 304 interfaces with an interior wall of a uterus during uterine sounding as determined based on tactile feedback provided by the support 402 disposed within the cavity 400 of the shaft 304. The interface between the shaft tip 308 and the wall of the uterus is atraumatic based on the rounded shape of the shaft tip 308 and the bending design of the elongated shaft 304. In other words, puncture or scratching is eliminated since the cervical dilator 300 is designed to slide the shaft tip 308 away from the wall of the uterus if excessive force is used in guiding the shaft 304.

In step 830, and once the shaft tip 308 interfaces with the interior wall of the uterus, the user will stop guiding the shaft 304 and will grasp an exterior surface of the shaft 304 of the cervical dilator 300 at a measurement location proximate an entrance of the cervix of the patient. The measurement location includes the markings 314 spaced along the exterior surface of the shaft 304. In other words, the user guides the shaft 304 through the cervix just until physical feedback is received that the shaft tip 308 has touched the distal uterine wall, and then uses finger to hold the shaft 304 at a location coincident with an entrance of the cervix of the patient.

In step 840, while continuing to grasp the exterior surface of the shaft of the cervical dilator at the measurement location, the user will remove the shaft 304 and the balloon 310 from the cervix of the patient until the markings 314 at a grasped portion of the measurement location can be viewed to determine a length or depth of the uterus. For example, the user can grasp the shaft 304 at a central-most marking 314c (see FIG. 5) that represents an 8 cm or average uterine depth. In another example, the user can grasp the shaft 304 at a marking 314a (see FIG. 5) closest to the balloon 310 that represents a 6 cm uterine depth. The user can remove any portion of the shaft 304 necessary to read the measurement as part of the uterine sounding method 800.

In step 850, the user can record the uterine depth measurement, completing the uterine sounding method 800. Recording the uterine depth measurement can include physical recordation, such as within a log or as part of surgical notes, verbal notation to another member of the user's medical team, or any other means of sufficiently capturing the uterine depth measurement to support further locating or positioning the cervical dilator 300 or another instrument to be used in a procedure related to the uterus within the cervical canal or endometrial canal. The uterine sounding method 800 described in FIG. 8 can be performed before cervical dilation as described in FIG. 9.

Figure 9:
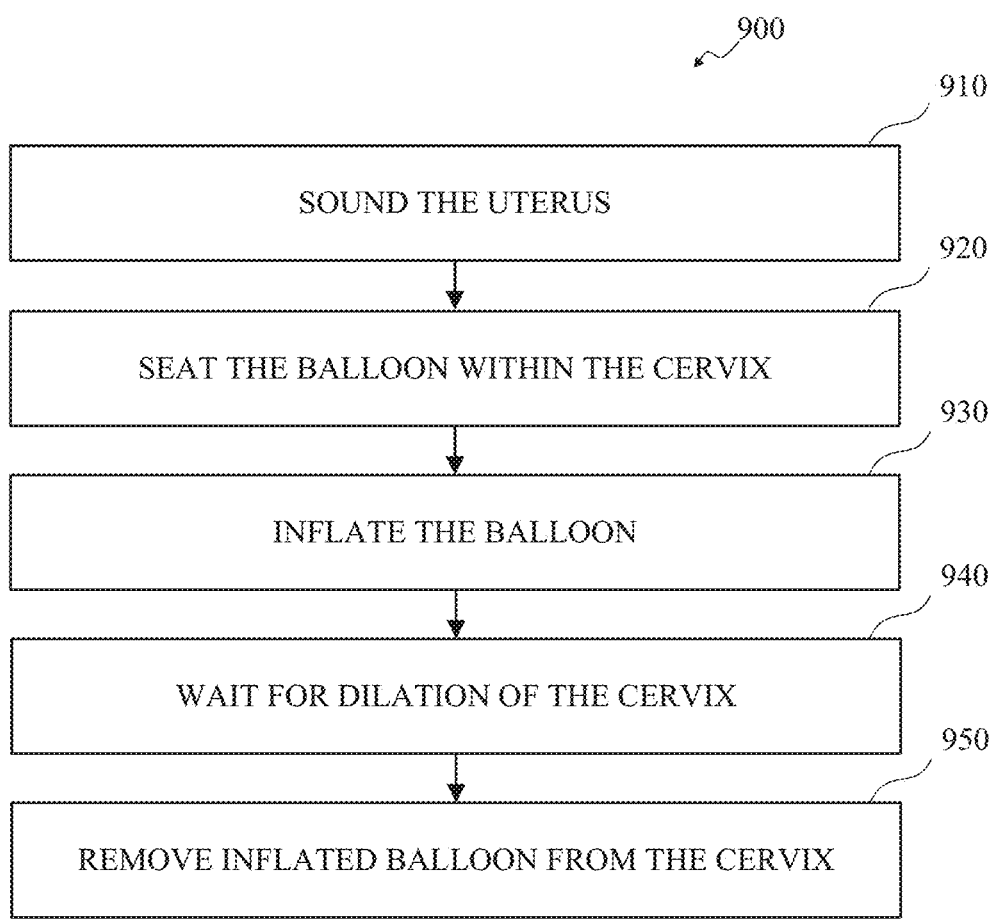
FIG. 9 shows a flowchart describing a cervical dilation method using the cervical dilator of FIG. 3.

FIG. 9 shows a flowchart describing a cervical dilation method 900 using the cervical dilator 300 of FIG. 3. In step 910, the cervical dilation method 900 includes the user sounding a uterus of a patient, for example, to determine its depth prior to additional procedures to be performed in the uterus in a manner described in the uterine sounding method 800 of FIG. 8. In step 920, and after sounding the uterus as described in step 910, the user guides the shaft 304 and the balloon 310 of the cervical dilator 300 through the cervix of the patient to a position sufficient to seat the balloon 310 in its uninflated state within the cervix. The balloon 310 can be seated when a distal end, e.g. the first end 500 shown in FIG. 5, is located in or near an entrance of the uterus and a proximal end, e.g. the second end 502, of the balloon 310 is located in or near an entrance of the cervix such that the balloon 310 fills a canal of the cervix.

In step 930, the user can inflate the balloon 310. Inflation of the balloon 310 is achieved by introducing a predetermined amount of fluid to the shaft inlet 306 of the cervical dilator 300 such that the fluid travels along the shaft cavity 400 (see FIG. 5), through the opening 312 in the shaft 304, and into the balloon cavity 600 (see FIG. 6) to fill the balloon to the inflated state. In one example, the predetermined amount of fluid can be 10 ml of air. In another example, the predetermined amount of fluid can be 20 ml of air. In a third example, the predetermined amount of fluid can be 15 ml of saline. The volume and type of fluid can be determined based on factors such as physical characteristics of the patient (e.g., age, uterine size, uterine depth, cervical pliancy, etc.) or details of further procedures to be performed (e.g., type, size, an number of instruments that require access the uterus). The time to introduce the predetermined volume of fluid can range from 5 seconds to 25 seconds or from 10 seconds to 20 seconds. This is greatly improved over a time needed to introduce the set of rods 12a-f described in reference to FIG. 1. Introduction, removal, and switching between the rods 12a-f of FIG. 1 can last from one to two minutes and is susceptible to user error as previously described.

In step 940, the user waits a predetermined time period to allow for cervical dilation while the balloon 310 is in the inflated state and seated within the cervix. For example, the user can wait between 5 seconds and 30 seconds or between 10 seconds and 20 seconds for the balloon 310 to dilate the cervix depending on physical characteristics of the patient or details of further procedures to be performed. Again, the cervical dilation method 900 using the cervical dilator 300 of FIGS. 3-7 is faster and less prone to user error or patient injury than use of the rods 12a-f of FIG. 1 that may take several minutes to complete.

In step 950, and after waiting the predetermined time period, the user can apply light tension to the exterior surface of the shaft 304 to remove the shaft 304 and the balloon 310 in the inflated state from the cervix of the patient. It is usually unnecessary to deflate the balloon 310, that is, to change the balloon 310 from the inflated state to the uninflated state, since once the cervix is dilated, the balloon 310 is easily removed from the cervix with light tension without abrasion or injury to the patient.

The cervical dilator 300 of FIGS. 3-7 provides an improved process for uterine sounding and cervical dilation over the rods 12a-f of FIGS. 1-2. The cervical dilator 300 is designed to be discarded after use, requires only one or two independent insertions into a cervix of the patient, is flexible and pliant to be atraumatic to the vagina, cervix, and uterus, and requires less time to achieve uterine sounding and cervical dilation than the rods 12a-f.

While the disclosure has been described in connection with certain embodiments, it is to be understood that the disclosure is not to be limited to the disclosed embodiments but, on the contrary, is intended to cover various modifications and equivalent arrangements included within the scope of the appended claims, which scope is to be accorded the broadest interpretation so as to encompass all such modifications and equivalent structures as is permitted under the law.

What is claimed is:

1. A method of cervical dilation using a cervical dilator including a shaft and a balloon sealed to the shaft, comprising:

guiding a shaft and the balloon of the cervical dilator through a cervix until a shaft tip at a first end of the shaft interfaces with an interior wall of a uterus during uterine sounding as determined based on tactile feedback provided by a support disposed within the shaft;

when the shaft tip interfaces with the interior wall of the uterus, stopping the guiding and grasping an exterior surface of the shaft of the cervical dilator at a measurement location while abutting a proximal end of the cervix, wherein the measurement location includes markings spaced along the exterior surface of the shaft;

while grasping the exterior surface of the shaft of the cervical dilator at the measurement location, removing the shaft and the balloon from the cervix until the markings at a grasped portion of the measurement location can be viewed to determine a length or depth of the uterus;

after determining the length or depth of the uterus, re-guiding the shaft and the balloon of the cervical dilator through the cervix to locate the balloon within the cervix, wherein a distal end of the balloon is fluidly sealed to the exterior surface of the shaft proximate the shaft tip and a proximal end of the balloon is fluidly sealed to the exterior surface of the shaft at a location proximate the markings, wherein the balloon defines a balloon cavity between an interior surface of the balloon and the exterior surface of the shaft;

wherein the shaft defines a shaft cavity extending from a shaft inlet along an interior surface of the shaft to the shaft tip, wherein the shaft defines an opening at a location between the distal and proximal ends of the balloon that is closer to the distal end of the balloon, wherein the opening fluidly couples the shaft cavity and the balloon cavity, and wherein seating the balloon includes locating the distal end of the balloon in or near a distal end of the cervix and locating the proximal end of the balloon in or near the proximal end of the cervix;

after locating the balloon within the cervix, introducing a predetermined amount of fluid to the shaft inlet such that the fluid travels along the shaft cavity, through the opening, and into the balloon cavity to inflate the balloon to an inflated state and seat the balloon within the cervix; and after inflating the balloon to the inflated state, waiting a predetermined time period to allow cervical dilation, then applying light tension to the exterior surface of the shaft to remove the shaft and balloon in the inflated state from the cervix.

2. The method of claim 1, wherein the location of the opening is between 15 percent and 35 percent of a distance from the distal end of the balloon to the proximal end of the balloon.

3. The method of claim 1, wherein the balloon is in an uninflated state without fluid within the balloon cavity when guiding the shaft and the balloon of the cervical dilator through the cervix during uterine sounding.

4. The method of claim 1, wherein a shape of the balloon in the inflated state includes the distal and proximal ends of the balloon having cone angles between 10 degrees and 30 degrees and a central portion of the balloon between the distal and proximal ends of the balloon having a generally cylindrical shape.

5. The method of claim 1, wherein the shaft tip is atraumatic.

6. The method of claim 5, wherein the fluid is introduced to the shaft inlet by an outlet of a syringe, and wherein the fluid is air.

7. The method of claim 6, wherein the predetermined amount of fluid ranges from 5 mL to 30 mL.

8. The method of claim 1, wherein the support is a wire formed from spring-tempered stainless steel, and wherein the wire extends from the shaft inlet to the shaft tip.

9. The method of claim 1, wherein the markings spaced along the exterior surface of the shaft indicate distance from the shaft tip.

10. The method of claim 9, wherein the markings along the exterior surface of the shaft alternate in thickness and indicate at least three of a distance of 6 cm, 7 cm, 8 cm, 9 cm, or 10 cm from the shaft tip.

11. A method of cervical dilation using a cervical dilator, comprising:
guiding a shaft and a balloon of the cervical dilator through a cervix to locate the balloon in an uninflated state within a cervix,
wherein the shaft extends from a shaft inlet to a shaft tip,
wherein a distal end of the balloon is fluidly sealed to an exterior surface of the shaft proximate the shaft tip and a proximal end of the balloon is fluidly sealed to the exterior surface of the shaft at a location spaced from the distal end and the shaft tip,
wherein the balloon defines a balloon cavity between an interior surface of the balloon and the exterior surface of the shaft;
wherein the shaft defines a shaft cavity extending from the shaft inlet along an interior surface of the shaft to the shaft tip,
wherein the shaft defines an opening at a location between 15 percent and 35 percent of a distance from the distal end to the proximal end of the balloon, and wherein the opening fluidly couples the shaft cavity and the balloon cavity, and
wherein locating the balloon includes locating the distal end of the balloon in or near a distal end of the cervix and locating the proximal end of the balloon in or near a proximal end of the cervix such that the balloon fills a canal of the cervix;

after locating the balloon within the canal of the cervix, introducing a predetermined amount of fluid to the shaft inlet such that the fluid travels along the shaft cavity, through the opening, and into the balloon cavity to fill the balloon to an inflated state to seat the balloon within the canal of the cervix; and while the balloon is in the inflated state, waiting a predetermined time period to allow cervical dilation; and after waiting the predetermined time period, applying light tension to the exterior surface of the shaft to remove the shaft and the balloon in the inflated state from the cervix.

12. The method of claim 11, wherein the fluid is air, wherein the predetermined amount of fluid ranges from 10 mL to 20 mL, wherein the predetermined time period ranges from 5 seconds to 30 seconds, and wherein a shape of the balloon in the inflated state includes a central portion of the balloon between the distal and proximal ends of the balloon having a generally cylindrical shape.

* * * * *